United States Patent [19]

Biddlecom et al.

[11] 4,336,404
[45] * Jun. 22, 1982

[54] 1-ACYLOXY-15-DEOXY-16-HYDROXY-ANALOGS OF PROSTAGLANDIN $E_1$

[75] Inventors: William G. Biddlecom; Harold C. Kluender; Warren D. Woessner, all of Madison, Wis.

[73] Assignee: Miles Laboratories, Inc., Elkhart, Ind.

[*] Notice: The portion of the term of this patent subsequent to Jan. 2, 1996, has been disclaimed.

[21] Appl. No.: 154,384

[22] Filed: May 29, 1980

Related U.S. Application Data

[63] Continuation of Ser. No. 38,640, May 14, 1979, abandoned.

[51] Int. Cl.³ .............................................. C07C 69/18
[52] U.S. Cl. ...................................... 560/231; 542/426
[58] Field of Search ......................................... 560/231

[56] References Cited

U.S. PATENT DOCUMENTS 4,026,151  5/1977  Grudzinkas ......................... 560/231
4,061,470 12/1977  Floyd, Jr. et al. .................. 560/231
4,132,738  1/1979  Kluender et al. ................... 560/121

Primary Examiner—Nicky Chan
Attorney, Agent, or Firm—Jerome L. Jeffers

[57] ABSTRACT

Disclosed are 1-acyloxy-15-deoxy-16-hydroxy prostaglandin $E_1$ analogs characterized by the formula:

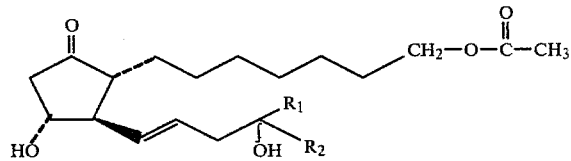

Compounds corresponding to the foregoing formula in which $R_1$ can be H or methyl and $R_2$ can be $C(CH_3)_2(CH_2)_2CH_3$ or $(CH_2)_3CH_3$ are variously useful as inhibitors of gastric secretion and as bronchodilators.

4 Claims, No Drawings

1-ACYLOXY-15-DEOXY-16-HYDROXY-ANALOGS OF PROSTAGLANDIN $E_1$

This is a continuation of application Ser. No. 038,640 filed May 14, 1979, now abandoned.

BACKGROUND OF THE INVENTION

1. Field of the Invention

The compounds of this invention are analogs of natural prostaglandins.

Natural prostaglandins are alicyclic compounds related to prostanoic acid, the structure of which is:

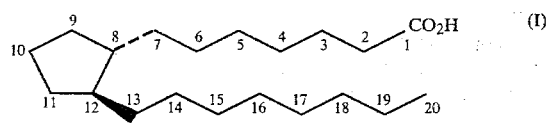

By convention, the carbon atoms of I are numbered sequentially from the carboxylic carbon atom. An important stereochemical feature of I is the transorientation of the sidechains $C_1$–$C_7$ and $C_{13}$–$C_{20}$, an orientation common to all prostaglandins. In I, as elsewhere in this specification, solid lines (—) provide a reference plane (such as the cyclopentyl ring or the bonds among $C_1$–$C_7$ and $C_{13}$–$C_{20}$); a dashed line (- - -) indicates projection of a covalent bond below such reference plane (alpha-configuration); while a wedged line (◀■) represents direction above such plane (beta-configuration). These conventions apply to all structural formulae subsequently discussed in this specification. In some structures, however, a swung dash or serpentine line ( ∼ ) denotes orientation of a covalent bond either above or below the plane of reference (indicated by the Greek letter xi in the nomenclature of such structures).

Natural prostaglandins have the general structure,

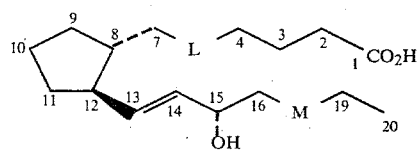

in which L and M may be ethylene or cis-vinylene radicals. Prostaglandins are characterized by the substituents on the cyclopentyl ring, the position of double bonds, if any, in the cyclopentyl ring and the number of double bonds in the side chains. When the cyclopentyl ring is fully saturated, carbonyl substituted at the 9-position and hydroxyl substituted at the 11-position an E-class prostaglandin is represented (PGE) and when there is a single double bond in the sidechains, i.e., L and M in Formula II are ethylene, a type-1 prostaglandin is represented. The naturally occurring E-class type 1 prostaglandin known as prostaglandin $E_1$ or $PGE_1$, is represented by the formula:

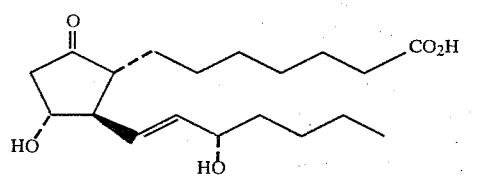

Formulae I, II and III depict the nat-isomer, i.e., the $C_7$–$C_8$ bond in the alpha-configuration and the $C_{12}$–$C_{13}$ bond in the beta-configuration. In the ent-isomer (which does not occur in nature), the direction of the bonds at $C_7$–$C_8$ and $C_{12}$–$C_{13}$ is reversed.

Recent research indicates that certain prostaglandins, including $PGE_1$ and analogs thereof, elicit biochemical and physiological effects in a variety of mammalian systems. For example, in rats, $PGE_1$ increases the release of growth hormone and in sheep it has been found to inhibit ovarian progesterone secretion. In mice, $PGE_1$ has been found to increase thyroid activity whereas in hypophysectomized rats it has been found to stimulate stereordogensis in the adrenal glands.

In the mammalian male reproductive system, $PGE_1$ contracts the smooth muscle of the vas deferens and in the female reproductive system PGE compounds contact uterine smooth muscle. Prostaglandins stimulate contraction of gastrointestinal smooth muscle in vivo and in vitro. In dogs, $PGE_1$ inhibits gastric secretion. In most mammalian respiratory tracts, PGE compounds affect in vitro preparation of tracheal smooth muscle. The human lung normally contains PGE compounds; consequently, some cases of bronchial asthma may involve an imbalance in the production or metabolism of these compounds.

In addition, prostaglandins are involved in certain hematic mechanisms in mammals. For example, $PGE_1$ inhibits aggregation of blood platelets in vitro. In a variety of mammalian cardiovascular systems, PGE compounds are vasodilators by virtue of their action on vascular smooth muscle.

Accordingly, it can be seen that prostaglandins and their analogs have broad clinical implications and research in this area continues in laboratories throughout the world.

2. Prior Art

U.S. Pat. No. 4,132,738 issued Jan. 2, 1979 discloses 15-deoxy-16-hydroxyprostaglandins of the structural formula:

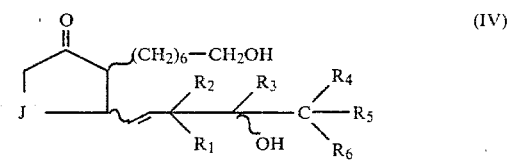

wherein J is R or S hydroxymethylene; $R_1$ is hydrogen; $R_2$ is hydrogen or together with $R_4$ is a methylene chain of 2 to 3 carbon atoms such that a cycloalkyl of 5 to 6 carbon atoms is formed; $R_3$ is hydrogen or methyl or together with $R_4$ is a methylene or a lower alkylated methylene chain of 2 to 5 carbon atoms such that a cycloalkyl or lower alkylated cycloalkyl of 4 to 7 carbon atoms is formed or together with $R_4$ forms a bicycloalkyl or bicycloalkenyl moiety. This patent also discloses $PGE_1$ ester analogs of compounds of the above formula limited to structures wherein two of $R_2$, $R_3$, $R_4$ and $R_5$ form a cycloalkyl, lower alkylated cycloalkyl, bicycloalkyl or bicycloalkenyl. These prostaglandin analogs selectively produce bronchodilation and decrease gastric secretion in vivo.

U.S. Pat. No. 3,965,143 issued June 22, 1976 is directed to 16-hydroxy prostaglandin analogs which are acids and esters represented by the structural formula:

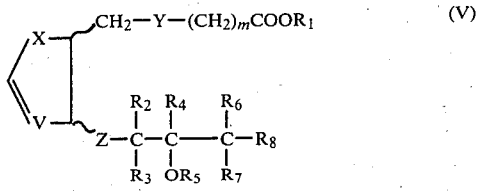

where $R_1$, $R_2$, $R_3$, $R_4$, $R_6$ and $R_7$ can be hydrogen or a lower alkyl radical and $R_8$ is an alkyl group containing 5 to 7 carbon atoms. In addition, this patent states that x can be carbonyl, V can be hydroxymethylene, Y can be ethylene and Z can be trans vinylene.

Netherlands Patent Application No. 73-10776, U.S. Application Ser. No. 274,769, discloses acids and esters of 16-hydroxy prostaglandin analogs represented by the structural formula:

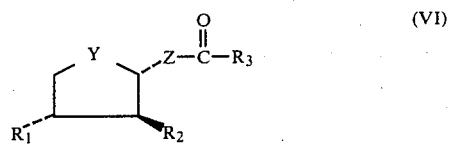

In the above formula $R_1$ can be hydroxy, Y can be carbonyl, Z can be polymethylene of 3 to 8 carbon atoms, $R_3$ can be hydroxy or an alkoxy group having from 1 to 12 carbon atoms and $R_2$ can be —CH═CH—$CH_2$—R″ where R″ can be a straight chain alkyl group having from 2 to 10 carbon atoms and substituted with a hydroxy or triphenylmethoxy group or a straight chain alkyl group having from 2 to 6 carbon atoms and having one branched alkyl group of from 1 to 3 carbon atoms and substituted with a hydroxy or triphenylmethoxy group.

SUMMARY OF THE INVENTION

The present invention involves 1-acyloxy-15-deoxy-16-hydroxy prostaglandin $E_1$ analogs characterized by the formula:

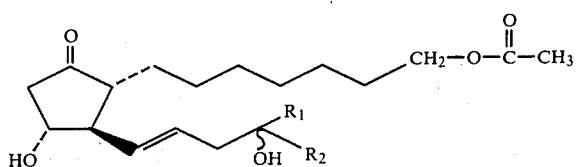

In the above formula $R_1$ is H or methyl and $R_2$ is $C(CH_3)_2(CH_2)_2CH_3$ or $(CH_2)_3CH_3$ provided that when $R_1$ is methyl, $R_2$ is $(CH_2)_3CH_3$ and when $R_1$ is H, $R_2$ is $C(CH_3)_2(CH_2)_2CH_3$.

Compounds corresponding to the foregoing formula are variously useful as inhibitors of gastric secretion and as bronchodilators.

DETAILED DESCRIPTION

The method of preparing the instantly claimed compounds is schematically set out in Scheme I, infra. Referring to Scheme I, the reaction of 4R-hydroxy-2-[7-hydroxyheptyl]-2-cyclopenten-1-one having the structural Formula VIII with acetic acid in an inert solvent, such as tetrahydrofuran, ether or toluene, and an acid catalyst such as para-toluene sulfonic acid, at a temperature of from 20° to 50° for 5 to 50 hours provides the compound having the structural Formula IX.

The hydroxyl group of Compound IX is protected by methods familiar to those skilled in the art (see: "Protective Groups In Organic Chemistry", J. F. W. McOmie (Ed.), Plenum Press, New York (1973)) to provide a compound of structural Formula X where E is an acid-labile hydroxyl-protecting group, specifically a tetrahydropyran-2-yl or 1-ethoxyethyl.

The reaction of the appropriate substituted 2-cyclopenten-1-one having the structural Formula X with the organolithiocuprate of Formula XI, wherein Lig represents a solubilizing ligand. Generally Lig is a tri-(dialkyamino)phosphine of 6-12 carbon atoms, trialkylphosphine having 3–12 carbon atoms, diarylphosphine, dialkylsulfide having 2–12 carbon atoms arylsulfide or di-(trialkylsilyl)amino having 6–12 carbon atoms. Specifically Lig can be a tri-(dimethylamino)phosphine, tri(n-butyl)phosphine, diphenylphosphine, diisopropylsulfide, dibutylsulfide, dimethylsulfide, diphenylsulfide or di(trimethylsilyl)amino group.

$R^r$ is iodide, thiophenylate, alkyn-1-yl having 3 to 8 carbon atoms or $R^t$;

$R^t$ is a radical having the formula:

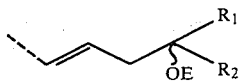

E is an acid-labile hydroxyl-protecting group, specifically a tetrahydropyran-2-yl or 1-ethoxyethyl.

$R_1$ is defined as H, or $CH_3$ $R_2$ is defined as $(CH_2)_3CH_3$ or $C(CH_3)_2(CH_2)_2CH_3$.

The compounds of the present invention, Formula VII, are prepared via the 1,4-conjugate addition of a 2-cyclopenten-1-one and an organolithiocuprate as reported by Sih, et al. (J. Amer. Chem. Soc., 97, 857 and 865 [1975] and references cited therein). The reaction between compounds of structural Formulae X and XI in an inert solvent such as ether, tetrahydrofuran, hexane, pentane or toluene, under an inert atmosphere such as nitrogen or argon, at a temperature of from −80° to +10° C., for about 0.25 to three hours provides the intermediate having the structural Formula XII.

Hydrolysis of the intermediate XII provides the prostaglandin VII. Chemical hydrolysis can be accomplished by treatment with weakly acidic water mixture, e.g. acetic acid-water (65:35 v/v) with 10% tetrahydrofuran, at a temperature of about 20° to 45° C. for about 0.5 to 48 hours.

All compounds of this invention can be isolated from reaction mixtures and purified by well-known organic chemistry procedures. For example, the compounds can be isolated by dilution of the reaction mixture with water, extraction with a water-immiscible solvent such as benzene, cyclohexane, ether, ethyl acetate, methylene chloride, toluene and the like; chromatography; distillation or a combination of these procedures. Purification of these compounds can be accomplished by methods which are well-known in the art for the purification of prostaglandins, lipids, fatty acids, and fatty esters. Such methods as reverse phase partition chromatography; counter-current distribution; adsorption chromatography on acid washed magnesium silicate, neutral or acid washed silica gel, alumina or silicic acid; preparative paper chromatography; preparative thin layer chromatography; high pressure liquid-liquid chromatography; gas-liquid chromatography; and combinations thereof can be used to purify the compounds produced by the processes of this invention.

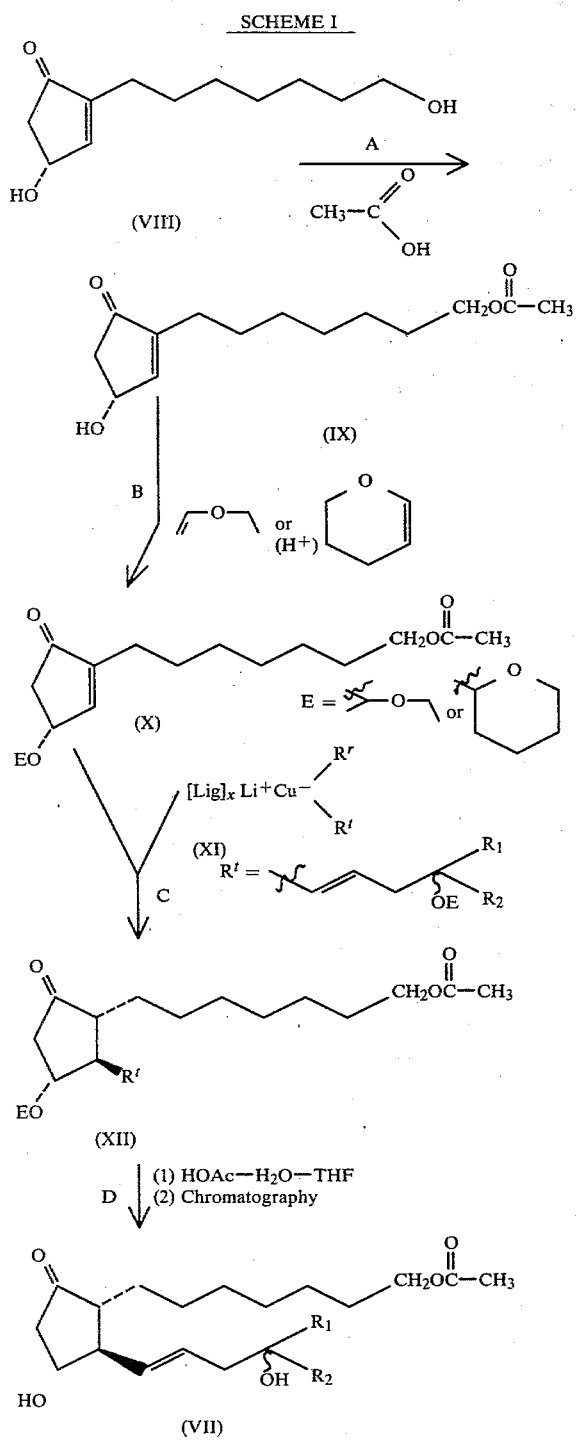

$R_1 = H, R_2 = C(CH_3)_2(CH_2)_2CH_3$ (TR-7039, TR-7040)
$R_1 = CH_3, R_2 = (CH_2)_3CH_3$ (TR-7015)

The preparation of the compounds of this invention is more specifically described in the following examples in which all temperatures are in °C. In the following examples NMR spectra were determined in CDCl₃ and infrared (ir) spectra in CHCl₃ unless otherwise noted. Analytical thin layer chromatography was performed on 0.2 mm Silica Gel 60 F254 plates and preparative thin-layer chromatography was performed using 2.0 mm Silica Gel 60 F254 plates. "System II" is defined as the organic layer from a mixture of ethyl acetate, acetic acid, isooctane, and water in a ratio of 11:2:5:10. Spots were visualized under uv light and/or by ceric sulfate spray reagent [See K. Schreiber, et al., J. Chromatography, 12, 63 (1962)]. Column chromatographic separations were performed on Silica Gel 60 using a hexane-ethyl acetate gradient elution unless otherwise specified. Mass spectra were determined by WARF, Inc., Madison, Wis.

EXAMPLE I

Preparation of
1-acetoxymethyl-11α,16S-dihydroxy-17,17-dimethyl-prost-13E-en-9-one (TR-7039) and
1-acetoxymethyl-11α,16R-dihydroxy-17,17-dimethyl-prost-13E-en-9-one (TR-7040)

(A) 4R-hydroxy-2-[7-hydroxyheptyl]-2-cyclopenten-1-one was prepared from the appropriate 2-(ω-hydroxyalkyl) cylopent-1,3,4-trione as described in *Tetrahedron Letters*, 2063 (1977).

(B) 4R-2-[7-acetoxyheptyl]-2-cyclopenten-1-one:

To a solution of 2.5 g of 4R-2-[7-hydroxyheptyl]-2-cyclopent-en-1-one in 6 ml of tetrahydrofuran and 28 mg of para-toluene sulfonic acid, was added 1.0 ml glacial acetic acid. The mixture was stirred for 40 hours at 36° C! and the solution reduced in volume by evaporation of solvents in vacuo. The oily residue was chromatographed (silica gel, 1:1 v/v hexane-ethyl acetate) to yield 1.9 g of 4R-2-[7-acetoxyheptyl]-2-cyclopenten-1-one as a yellow oil, $R_f$(System II) 0.44. The material had the following spectral characteristics:

Analysis: NMR (CDCl₃) δ 1.1–2.0 (m, 10H), 2.05 (3H, s), 2.2 (m, 2H), 2.85 (2H, ddd, J=18, 6, 6 Hz), 3.45 (bm, OH), 4.1 (2H, t, J=7 Hz), 5.0 (1H, m), 7.25 (1H, m);ir (CHCl₃) 3600 (s), 3450 (b), 2945, 1710, 1635, 1025 cm⁻¹; MS m/e 254 (p), 236 (p—H₂O), 194 (p-HOAc); [α]$_D$+10.7° (c 1.31, CHCl₃).

(C) 4R-(Tetrahydropyran-2-yloxy)-2-[7-acetoxyheptyl]-2-cyclopenten-1-one was prepared from the acid catalyzed treatment of 4R-hydroxy-2-[7-acetoxyheptyl]-2-cyclopenten-1-one with dihydropyran.

Analysis: NMR (CDCl₃) δ 1.1–2.0 (16H, m), 2.05 (3H, s), 2.2 (2H, m), 2.6 (2H, m, ddd, J=13, 3, 1 Hz), 3.65 (2H, bt), 4.1 (2H, t, J=7 Hz), 4.9 (2H, m), 7.3 (1H, m); [α]$_D$+19.9° (c 1.03, CHCl₃); $R_f$(system II) 0.71.

(D) 4R-(1-Ethoxyethoxy)-2-[7-acetoxyheptyl]-2-cyclopenten-1-one was prepared from acid catalyzed treatment of 4R-hydroxy-2-[7-acetoxyheptyl]-2-cyclopenten-1-one with ethyl vinyl ether.

Analysis: NMR (CDCl₃)₃ δ 1.1–2.0 (16H, m), 2.1 (3H, s), 2.2 (2H, m), 2.85 (2H, ddd, J=20, 6, 6 Hz), 3.65 (q, J7 Hz), 4.1 (2H, t, J=7 Hz), 4.95 (2H, bm), 7.3 (1H, m); ir (CHCl₃) 3000, 2940, 1715, 1460, 1120 cm⁻¹; [α]$_D$+1,7° (c 1.24, CHCl₃).

(E) Preparation of organolithiocuprate from protected iodovinylalcohol—A solution of 348 mg (1.02 mmol) 1-iodo-4RS-(ethoxy-1-ethoxy)-5,5-dimethyl-oct-1E-ene, prepared as described in Example 3 of U.S. Pat. No. 4,132,738 utilizing ethyl vinyl ether in lieu of dihydropyran as the iodovinyl alcohol protecting reagent, in 2 ml. of dry ether was stirred in a flask under argon with −78° bath cooling as 1.3 ml (2.04 mmol) of a 1.56 M solution of t-butyllithium in pentane was added dropwise via syringe.

A second solution was prepared by stirring under argon a suspension of 0.133 g (1.02 mmol) of dry copper (I) pentyne in 2 ml of dry ether solubilized with 0.39 ml of hexamethylphosphorous triamide until it became homogeneous. This second solution was then transferred via syringe to the above alkenyllithium reaction mixture as it was stirred with −70° bath cooling. The desired lithiocuprate reagent, an orange mixture, was stirred for 15 minutes after the addition was complete.

(F) The synthesis of the above-entitled prostaglandin E$_1$ analogs was achieved as follows:

A solution of 237 mg (0.70 mmol) of 4R-(tetrahydropyran-2-yloxy)-2-(7-acetoxy heptyl)-2-cyclopenten-1-one in 1.0 ml of dry ether was added to the lithiocuprate reaction mixture described in the preceding step as stirring was continued at −78° C. After addition was complete, the resultant orange mixture was stirred for 10 minutes at −78° and then at −20° for two hours.

The reaction mixture was quenched at −20° by the addition of sufficient two percent sulfuric acid to give an acidic aqueous phase after stirring. The resultant mixture was thoroughly shaken and then filtered through Celite. The filter pad was rinsed thoroughly with ether whereupon the filtrate phases were separated and the organic phase was washed with saturated aqueous sodium bicarbonate and brine. It was then dried over MgSO$_4$ and evaporated in vacuo to yield 386 mg of an orange oil.

The residue from the preceding step was dissolved in 10 ml of acetic acid-water-THF (65:35:10) and left to stir under argon for 18 hours at room temperature. The residue was dissolved in ethyl acetate and washed with saturated aqueous sodium bicarbonate. The solution was back extracted with ethyl acetate whereupon the combined extract was dried over MgSO$_4$ and evaporated in vacuo to yield 293 mg of an orange oil. This oil was column chromatographed on silica gel (0.032–0.063 mm mesh size) with 1:1 (v/v) n-hexane-ethyl acetate to yield 7.1 mg of the pure PGE$_1$ analog designated as TR-7039 and 7.1 mg of the pure PGE$_1$ analog designated as TR-7040.

Analysis: (TR-7039) $[\alpha]_D$ −39.3° (c 0.62, CHCl$_3$); R$_f$ (System II) 0.51; nmr (CDCl$_3$) δ 0.90 (9H, bs), 1.1–2.0 (18H, m), 2.1 (3.0H, s), 2.15–3.1 (5H, m), 3.4 (1H, dd, J=6, 5 Hz), 4.1 (4H, bt), 5.65 (2H, m); ir (CHCl$_3$) 3600 (sharp), 3550–3200 (broad), 2940, 1730, 1460, 1255, 1065, 965 cm$^{-1}$; ms (C.I.) 411 (p+1), 393 (411-H$_2$O, base peak), 375 (411-2H$_2$O). (TR-7040) $[\alpha]_D$ −43.3° (c 0.20, CHCl$_3$); R$_f$ (System II) 0.49; nmr, ir and ms essentially identical to TR-7039.

EXAMPLE II

Preparation of 1-acetoxymethyl-11α,116RS-dihyroxy-16-methylprost-13E-en-9-one (TR-7015)

(A) Preparation of Organolithiocuprate from protected iodovinylalcohol:

(1) A solution of 804 mg (2.36 mmol) of 1-iodo-4-methyl-4RS-(ethoxy-1-ethoxy)-oct-1E-ene, prepared as described in Example 1B of U.S. Pat. No. 4,132,738, utilizing ethyl vinyl ether in lieu of dihydropyran as the iodovinyl alcohol, protecting reagent, in 4 ml of dry ether was stirred in a flask under argon with −78° bath cooling as 3.0 ml (4.73 mmol) of a 156 M solution of t-butyllithium in pentane was added dropwise via syringe. The resultant solution was stirred at −78° for two hours.

(2) A second solution was prepared by stirring under argon a suspension of 0.307 g (2.36 mmol) of dry copper (I) pentyne in 4 ml of dry ether solubilized with 0.90 ml of hexamethylphosphorous triamide, until it became homogeneous. This second solution was then transferred via syringe to the above alkyl lithium reaction mixture as it was stirred with −78° bath cooling. The desired lithiocuprate reagent, an orange mixture, was stirred for 15 minutes after the addition was complete.

(B) Repeating in a similar manner the procedure for preparing TR-7039 and TR-7040, but replacing 4R-(tetrahydropyran-2-yloxy)-2-(7-acetoxyheptyl)-2-cyclopenten-1-one and subsequent reaction with the copper complex prepared in step A provided the prostaglandin analog TR-7015 which was isolated as an oil.

Analysis: (TR-7015) $[\alpha]_D$ −59.8° (c 1.26, CHCl$_3$); R$_f$ (System II) 0.43; nmr (CDCl$_3$) δ 0.95 (3H, bt), 1.2 (3H, s), 1.1–1.9 (20H, m), 2.1 (3H, s), 2.15–2.9 (6H, m), 4.1 (3H, bt), 5.6 (2H, m); ir (CHCl$_3$) 3600 (sharp), 3550–3300 (broad), 2940, 1735, 1460, 1245, 1070, 965$^{-1}$; ms (C.I.) 397 (p+1) (379-H$_2$O, base peak) 361 (379-H$_2$O).

Biological Activity

A. In order to determine its potential utility in the treatment of ulcers, TR-7015 was tested to determine its effects on the gastric secretion in the rat. The details of this protocol are disclosed in the aforementioned U.S. Pat. No. 4,132,738. The compound was determined to have an activity value of 4 indicating a 76–100% decrease in gastric secretion.

B. As a preliminary screen to determine its potential utility in the treatment of asthma, TR-7040 was evaluated to determine its effect on the guinea pig trachea in vitro using the protocol described in U.S. Pat. No. 4,132,738. The compound was determined to have an activity value of 3 indicating that its ED$_{50}$, i.e., dose required to produce a response 50% that of carbachol, is in the range of 0.01 to 0.1 mcg/ml. This represents a mean relative potency of 0.3 based on a potency value of 1 for PGE$_1$.

TR-7040 was also tested for its effect on human bronchial muscle in vitro. In this test spirals of bronchial muscle are cut from apparently normal lung tissue obtained from surgery of carcinoma of the lung and stored overnight at 0°–4° C. in Krebs-Henseleit solution. On the following day, each spiral was suspended in a 10 ml bath aerated with 5 percent carbon dioxide in oxygen. The muscle was allowed to equilibrate for 90 minutes before the experiment began. The test drug was left in contact with the preparation for 5 minutes before a 30 second washout period. Responses were measured using a Harvard isotonic transducer with a load of 250 mg. The test compound was found to relax human bronchial muscle by a mean relative potency of 0.1 based on a potency value of 1 for PGE$_1$.

PGE$_1$ is very effective in relaxing the tracheobronchial muscle of experimental animals and of man and lessens the contraction of human bronchial muscle elicited by PGF$_{2\alpha}$. Administered by aerosol, PGE$_1$ is much more potent in causing relaxation of tracheobronchial muscle in guinea pigs and cats than isoprenaline. Based on these findings, it was suggested that PGE$_1$, if inhaled as an aerosol, could be clinically useful as a bronchodilator in treatment of human asthma. When tested clinically, PGE$_1$ indeed proved to be a potent bronchodilator in humans, however, it was found to elicit sufficient cough and sore throat to preclude its clinical use. Because of the cough problem inherent in the use of $PGE_1$ in the treatment of asthma, there has been a search for prostaglandin analogs which exhibit the ability to relax tracheobronchial muscle without causing sufficient cough to render the drug clinically unuseable. A prostaglandin which is less potent in relaxing the tracheobronchial muscle than $PGE_1$ would be more useful than $PGE_1$ in the treatment of asthma if it did not possess the undesirable side effect of eliciting cough in the individual being treated.

A novel method of testing for prostaglandin induced tracheobronchial irritancy has been developed. In this method, specific pathogen free cats (category III) of either sex are used. Conscious cats are placed in an adjustable Perspex chamber with a seal around the neck. The respiratory pattern and rate of each cat is recorded via a Fleisch head pneumotachograph protruding into the top of the chamber. Sound is recorded by a microphone also protruding into the chamber. An aerosol of 1–8 μm particle size is generated by a Monaghan 670 Ultrasonic nebuliser and passed to the cats face via an opening in the front of the chamber. Initially, each cat is challenged for 10 minutes with an aerosol of isotonic saline adjusted with phosphate buffer to pH 7.2 plus the appropriate concentration of ethanol. This control challenge is followed one minute later by a 10 minute aerosol challenge of the test compound in an appropriate vehicle and the test compound tested in the cat using increasing aerosol stock solution concentrations. A minimum of 3 days is left between challenges to avoid the development of tolerance to coughs.

Use of the foregoing procedure with TR-7040 as the test compound, demonstrated that its mean relative potency was 0.005 based on a potency value of 1 for $PGE_1$, i.e., TR-7040 is $5\times10^{-3}$ less potent than $PGE_1$ in its tendency to cause cough.

What is claimed is:

1. 1-acyloxy-15-deoxy-16-hydroxy-prostaglandin $E_1$ analogs characterized by the formula:

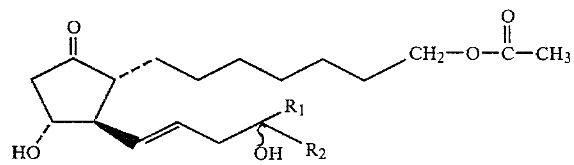

wherein $R_1$ is H or methyl and $R_2$ is $C(CH_3)_2(CH_2)_2CH_3$ or $(CH_2)_3CH_3$ provided that when $R_1$ is methyl, $R_2$ is $(CH_2)_3CH_3$ and when $R_1$ is H, $R_2$ is $C(CH_3)_2(CH_2)_2CH_3$.

2. A compound as defined by the formula in claim 1 wherein $R_1$ is H and $R_2$ is $C(CH_3)_2(CH_2)_2CH_3$.

3. A compound as defined by the formula in claim 1 wherein $R_1$ is methyl and $R_2$ is $(CH_2)_3CH_3$.

4. A compound as defined by the formula in claim 1 wherein $R_1$ is H, $R_2$ is $C(CH_3)_2(CH_2)_2CH_3$ and the 16-hydroxyl group is in the R configuration.

* * * * *